United States Patent
Li et al.

(10) Patent No.: US 10,889,748 B2
(45) Date of Patent: Jan. 12, 2021

(54) PROCESS FOR PREPARING DIBENZYLAMINE QUATERNARY AMMONIUM SALT HIGH-TEMPERATURE RESISTANT CORROSION INHIBITOR AND APPLICATIONS THEREOF

(71) Applicant: Southwest Petroleum University, Sichuan (CN)

(72) Inventors: Yongming Li, Sichuan (CN); Dingli Wang, Sichuan (CN); Youshi Jiang, Sichuan (CN); Xiyu Chen, Sichuan (CN); Juhui Zhu, Sichuan (CN)

(73) Assignee: SOUTHWEST PETROLEUM UNIVERSITY, Sichuan (CN)

( * ) Notice: Subject to any disclaimer, the term of this patent is extended or adjusted under 35 U.S.C. 154(b) by 0 days.

(21) Appl. No.: 16/622,673

(22) PCT Filed: Nov. 20, 2018

(86) PCT No.: PCT/CN2018/116451
§ 371 (c)(1),
(2) Date: Dec. 13, 2019

(87) PCT Pub. No.: WO2020/082476
PCT Pub. Date: Apr. 30, 2020

(65) Prior Publication Data
US 2020/0339865 A1     Oct. 29, 2020

(30) Foreign Application Priority Data

Oct. 23, 2018 (CN) .......................... 2018 1 1240768

(51) Int. Cl.
| | | |
|---|---|---|
| *C09K 8/54* | (2006.01) | |
| *C07C 209/84* | (2006.01) | |
| *C23F 11/14* | (2006.01) | |
| *E21B 41/02* | (2006.01) | |

(52) U.S. Cl.
CPC .............. *C09K 8/54* (2013.01); *C07C 209/84* (2013.01); *C23F 11/143* (2013.01); *E21B 41/02* (2013.01); *C09K 2208/32* (2013.01)

(58) Field of Classification Search
CPC .... C07C 209/84; C09K 2208/32; C09K 8/54; C23F 11/143; E21B 41/02
See application file for complete search history.

(56) References Cited

U.S. PATENT DOCUMENTS

2011/0269650 A1   11/2011   Hernandez Altamirano et al.

FOREIGN PATENT DOCUMENTS

| CN | 101365767 A | 2/2009 |
|----|-------------|--------|
| CN | 102887871 A | 1/2013 |
| CN | 106957281 A | 7/2017 |
| WO | WO2008157234 A2 | 12/2008 |

*Primary Examiner* — Jafar F Parsa
(74) *Attorney, Agent, or Firm* — Muncy, Geissler, Olds & Lowe, P.C.

(57) ABSTRACT

The present invention discloses a process for preparing a dibenzylaminquaternary ammonium salt high-temperature resistant corrosion inhibitor and applications thereof. The preparation process comprises the following steps: (1) Dissolve the amine reagents benzylamine, phenethylamine, morpholine or indole in an organic solvent, slowly add epichlorohydrin dropwise, stir to react at a room temperature for 12-14 hours, and then distill under reduced pressure, and wash to obtain an intermediate I; (2) Dissolve the intermediate I in an organic solvent, add dibenzylamine at a ratio, then add an acid binding agent, warm to 60-80° C. to react for 14 to 16 hours, after cooling to room temperature, perform filtration, extraction and distillation under a reduced pressure to obtain an intermediate II; (3) Dissolve the intermediate II in an organic solvent, add quaternizing reagent at a ratio, then warm to 80-110° C. to react for 12 to 15 hours, after cooling to room temperature, perform filtration, extraction and distillation under a reduced pressure to obtain the dibenzylaminquaternary ammonium salt high-temperature resistant corrosion inhibitor. The process is simple and feasible, and its principle is reliable, and the prepared corrosion inhibitor has good resistance to the acid corrosion of carbon steels in oil-gas wells.

9 Claims, No Drawings

PROCESS FOR PREPARING DIBENZYLAMINE QUATERNARY AMMONIUM SALT HIGH-TEMPERATURE RESISTANT CORROSION INHIBITOR AND APPLICATIONS THEREOF

TECHNICAL FIELD

The present invention relates to a process for preparing a dibenzylaminquaternary ammonium salt high-temperature resistant corrosion inhibitor in the field of corrosion inhibitor materials and applications thereof.

BACKGROUND ART

In the production-increasing and upgrading of oil-gas field, fracture acidification has become the mainstream method for the oil-gas field. In the acid fracturing and pickling process, the acid liquid can remove the blockage of the oil and gas wellbore to a great extent and improve the matrix permeability, thereby increasing the oil and gas recovery. However, the presence of acid liquid will also bring many problems to the oil field. The injection of acid liquid may cause corrosion of oil-gas well pipes and downhole metal equipment during the acidification process, and in severe cases, it may lead to sudden fracture accidents of downhole pipes, with potential safety hazards; in addition, the metal iron ions that are corroded by the acid solution may cause damage to the stratum. In order to prevent acid liquid from corroding equipment such as oil pipes, casings, etc., it is necessary to add a corrosion inhibitor to the acid liquid, which is the most commonly used and effective anti-corrosion measure. At present, most of the commercially available corrosion inhibitors have the drawbacks of easy coking, delamination, unstable dissolution and dispersion properties, and complicated preparation when under a high temperature.

In the invention titled "A composite type imidazoline quaternary ammonium salt corrosion inhibitor and preparation process thereof" (201410360217.3), the corrosion inhibitor contains (by weight percent): 30 wt % to 35 wt % of imidazoline alkylate quaternary ammonium salt, 8 wt % % to 10 wt % of nitrogen-containing organic polyphosphate, 1 wt % to 2 wt % of amphoteric surfactant, 0.5 wt % to 1 wt % of dispersant, 1 wt % to 2 wt % of co-solvent, and water. The corrosion inhibitor has a corrosion inhibition rate of greater than 70% when the dosage is 50 ppm in 50° C. self-made simulated water. It can be used in oil-gas wells, gathering and transportation systems and water injection processes in the oil fields, but its formula is complex, with high cost; in addition, it is not good for the environment.

In the invention titled "Synthesis process of a water-soluble imidazoline quaternary ammonium salt corrosion inhibitor" (201310524689.3), organic acids and organic amines are used as raw materials, to synthesize amide through amidation reaction first, then imidazoline is obtained through amide cyclization reaction, finally oil-soluble imidazoline is quaternized by a quaternizing agent such as dimethyl phosphite to synthesize water-soluble imidazoline quaternary ammonium salt corrosion inhibitor. The evaluation testes showed that the product has good water solubility and high corrosion inhibition rate, but its preparation process is complicated and the reaction temperature is as high as over 200° C.

Therefore, it is of great significance to develop a new type of high-temperature-resistant corrosion inhibitor with simple formula, mild synthesis conditions and meeting the rigor requirements of the current acidification construction of oil-gas wells.

SUMMARY OF THE INVENTION

An object of the present invention is to provide a process for preparing a dibenzylaminquaternary ammonium salt high-temperature resistant corrosion inhibitor and applications thereof. The process is simple and feasible, and its principle is reliable. The prepared corrosion inhibitor has good corrosion resistance at high temperature, and it has good solubility in aqueous hydrochloric acid solution; in addition, it can obviously inhibit the acid corrosion of carbon steels in oil-gas wells.

In order to achieve the foregoing technical object, the present invention adopts the following technical solutions:

A process for preparing a dibenzylaminquaternary ammonium salt high-temperature resistant corrosion inhibitor, comprising the following steps in sequence:

(1) Dissolve the amine reagents benzylamine, phenethylamine, morpholine or indole in an organic solvent, slowly add epichlorohydrin dropwise, stir to react at a room temperature for 12-14 h, and then distill under reduced pressure, and wash to obtain an intermediate I;

(2) Dissolve the intermediate I in an organic solvent, add dibenzylamine at a ratio, then add an acid binding agent, warm to 60-80° C. to react for 14 to 16 hours, after cooling to room temperature, perform filtration, extraction and distillation under a reduced pressure to obtain an intermediate II;

(3) Dissolve the intermediate II in an organic solvent, add quaternizing reagent at a ratio, then warm to 80-110° C. to react for 12 to 15 hours, after cooling to room temperature, perform filtration, extraction and distillation under a reduced pressure to obtain the dibenzylaminquaternary ammonium salt high-temperature resistant corrosion inhibitor.

Further, the molar ratio of epichlorohydrin to amine reagents is 1:1-1:3.

Further, the dropping rate of epichlorohydrin is 5-10 mL/min.

Further, the organic solvent is acetone, ethanol, or acetonitrile.

Further, the acid binding agent is potassium carbonate, sodium hydroxide or triethylamine.

Further, the molar ratio of dibenzylamine to the acid binding agent is 1:1-1:2.

Further, the molar ratio of dibenzylamine to the intermediate I is 1:1-1:4.

Further, the quaternizing agent is benzyl chloride, chloromethylnaphthalene or bromohexane.

Further, the molar ratio of the quaternizing reagent to the intermediate II is 1:1-2:1.

Applications of the dibenzylaminquaternary ammonium salt high-temperature resistant corrosion inhibitor mean that the corrosion inhibitor is used as an oil-gas well corrosion inhibitor, to show a significant inhibitory effect on the acid corrosion of carbon steels in oil-gas wells.

The preparation process of the invention is simple, and its mechanism is as follows: the epichlorohydrin chlorine atom and nitrogen atom on dibenzylamine have high activity, under the above reaction conditions, a ring opening reaction occur between epichlorohydrin and benzylamine, phenethylamine, morpholine or indole to get an intermediate I, then the chlorine atom on intermediate I reacts with dibenzylamine to obtain a tertiary amine. During the process, an acid binding agent must be added to prevent the reaction of generated hydrogen chloride and dibenzylamine from forming a dibenzylamine hydrochloride, so the tertiary amine product cannot be obtained to prevent the next quaternization process. After the tertiary amine is obtained, a quaternizing agent is added to obtain the dibenzylaminquaternary ammonium salt corrosion inhibitor. The corrosion inhibitor prepared contains multiple benzene rings and has multiple nitrogen atoms and oxygen atoms. The nitrogen atoms and oxygen atoms have lone pair electrons, and can form hybrid orbits with empty orbitals on iron atoms, with strong adsorption between them. The six-membered benzene ring has a large π-bond structure, can also hybridize with iron to tightly adsorb on iron, and inhibit its corrosion; in addition, multiple hydroxyl groups in the inhibitor molecule can greatly improve the dispersibility of the corrosion inhibitor and its solubility in acid solution. The corrosion inhibitor has good corrosion inhibition performance at high temperature. When used as an oil-gas well corrosion inhibitor, it has a significant inhibitory effect on the acid corrosion of carbon steels in oil-gas wells.

DETAILED DESCRIPTION OF THE PREFERRED EMBODIMENTS

The present invention is further described in conjunction with the following embodiments.

Embodiment 1

A process for preparing a dibenzylaminquaternary ammonium salt high-temperature resistant corrosion inhibitor, comprising the following steps:

(1) Add 8.71 g of morpholine to a 250 mL three-necked flask, and add 80 mL of absolute ethanol as a solvent at the same time, and then stir them evenly;

(2) Weigh 9.25 g of epichlorohydrin and dissolve in 30 mL of absolute ethanol, stir slowly, then add it to the morpholine solution dropwise slowly, stir to react at room temperature for 14 h, to obtain an intermediate I after distillation under reduced pressure;

(3) Weigh 1.79 g of intermediate I into a 250 mL three-necked flask, and add 90 mL of absolute ethanol as a solvent at the same time, then stir them evenly; weigh 1.97 g of dibenzylamine and dissolve in 30 mL of absolute ethanol, stir well, and slowly add dropwise to the intermediate I solution, then add 1.4 g of potassium carbonate, warm to 80° C. for reflux to react 14 h, after the reaction, cool to the room temperature, and perform filtration, extraction and distillation under a reduced pressure to obtain the intermediate II;

(4) Weigh 3.76 g of intermediate II into a 250 mL three-necked flask, add 100 mL of absolute ethanol as a solvent at the same time, then stir them evenly; weigh 1.76 g of chloromethylnaphthalene and slowly add dropwise to the intermediate II solution, then warm to 80° C. for reflux to react 13 h, after the reaction, cool to the room temperature, and perform filtration, extraction and distillation under a reduced pressure to obtain the dibenzylaminquaternary ammonium salt corrosion inhibitor.

The specific reaction process of the above preparation process is as follows:

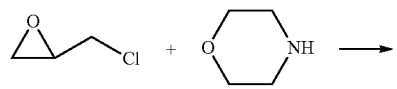

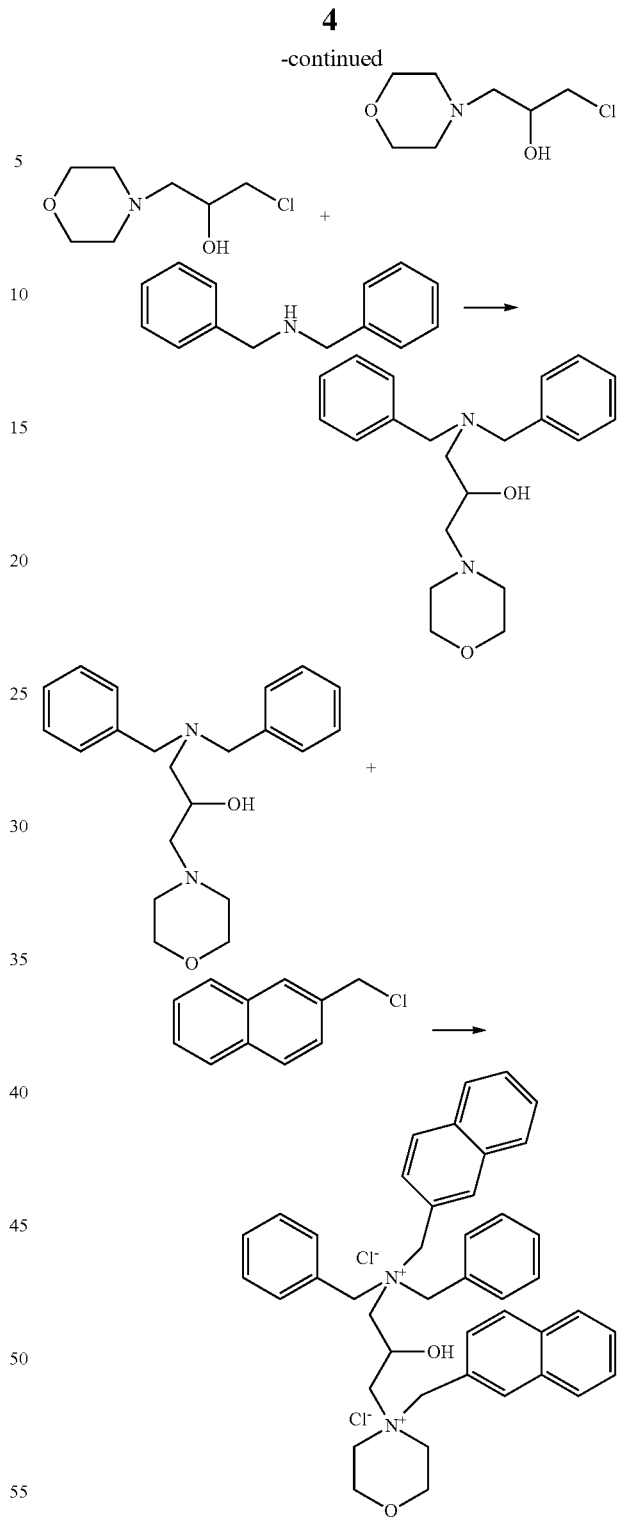

Embodiment 2

A process for preparing a dibenzylaminquaternary ammonium salt high-temperature resistant corrosion inhibitor, comprising the following steps:

(1) Add 5.59 g of indole to a 250 mL three-necked flask, and add 70 mL of acetone as a solvent at the same time, and then stir them evenly;

(2) Weigh 4.62 g of epichlorohydrin and dissolve in 30 mL of acetone, stir slowly, add dropwise to the above indole solution slowly, stir to react at room temperature for 12 h, to obtain an intermediate I after distillation under reduced pressure;

(3) Weigh 2.11 g of intermediate I into a 250 mL three-necked flask, and simultaneously add 90 mL of acetonitrile as a solvent, then stir them evenly; weigh 1.97 g of dibenzylamine in 30 mL of acetonitrile and stir well. Slowly add dropwise to the intermediate I solution, then add 1.2 g of triethylamine, warm to 57° C. for reflux to react 15 h, after the reaction, cool to the room temperature, and perform filtration, extraction and distillation under a reduced pressure to obtain the intermediate II;

(4) Weigh 4.08 g of intermediate II into a 250 mL three-necked flask, add 100 mL of anhydrous acetonitrile as a solvent at the same time, then stir them evenly, weigh 1.26 g of benzyl chloride and slowly add dropwise to the intermediate II solution, then warm to 85° C. for reflux to react 14 h, after the reaction, cool to the room temperature, and perform filtration, extraction and distillation under a reduced pressure to obtain the dibenzylaminquaternary ammonium salt corrosion inhibitor.

The specific reaction process of the above preparation process is as follows:

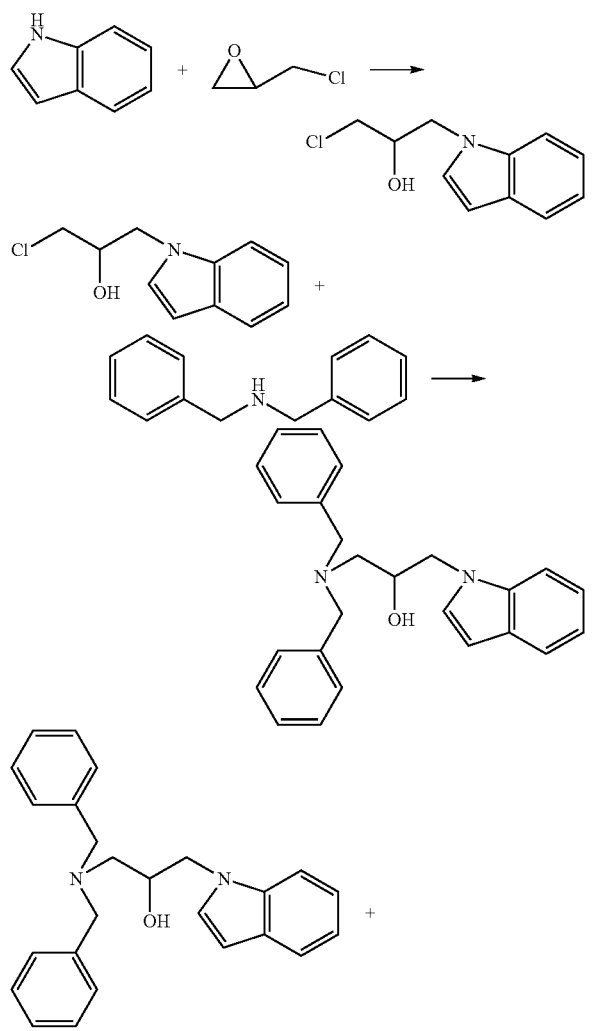

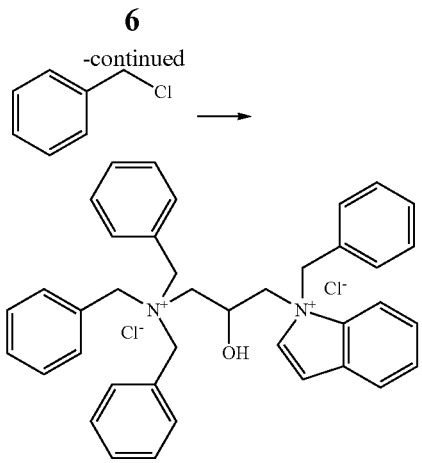

Embodiment 3

A process for preparing a dibenzylaminquaternary ammonium salt high-temperature resistant corrosion inhibitor, comprising the following steps:

(1) Add 10.82 g of benzylamine to a 250 mL three-necked flask, and add 100 mL of absolute ethanol as a solvent at the same time, and then stir them evenly;

(2) Weigh 9.25 g of epichlorohydrin and dissolve in 30 mL of absolute ethanol, stir slowly, then add it to the benzylamine solution dropwise slowly, stir to react at room temperature for 12 h, to obtain an intermediate I after distillation under reduced pressure;

(3) Weigh 2.07 g of intermediate I into a 250 mL three-necked flask, and add 90 mL of acetone as a solvent at the same time, then stir them evenly; Weigh 1.97 g of dibenzylamine and dissolve in 30 mL of acetone and stir well. and slowly add dropwise to intermediate I solution, then add 0.7 g of sodium hydroxide to the solution, warm to 60° C. for reflux to react 13 h, after the reaction, cool to the room temperature, and perform filtration, extraction and distillation under a reduced pressure to obtain the intermediate II;

(4) Weigh 4.04 g of intermediate II into a 250 mL three-necked flask, add 100 mL of absolute ethanol as a solvent at the same time, then stir them evenly; weigh 1.65 g of bromohexane and slowly add dropwise to the intermediate II solution, then warm to 80° C. for reflux to react 15 h, after the reaction, cool to the room temperature, and perform filtration, extraction and distillation under a reduced pressure to obtain the dibenzylaminquaternary ammonium salt corrosion inhibitor.

The specific reaction process of the above preparation process is as follows:

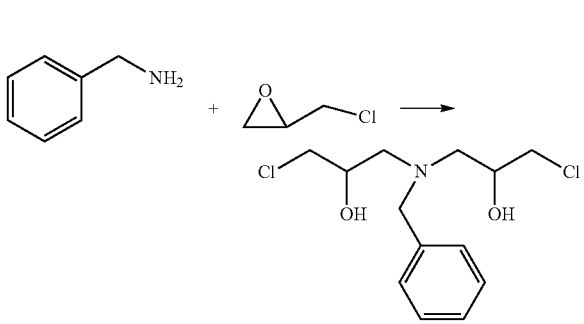

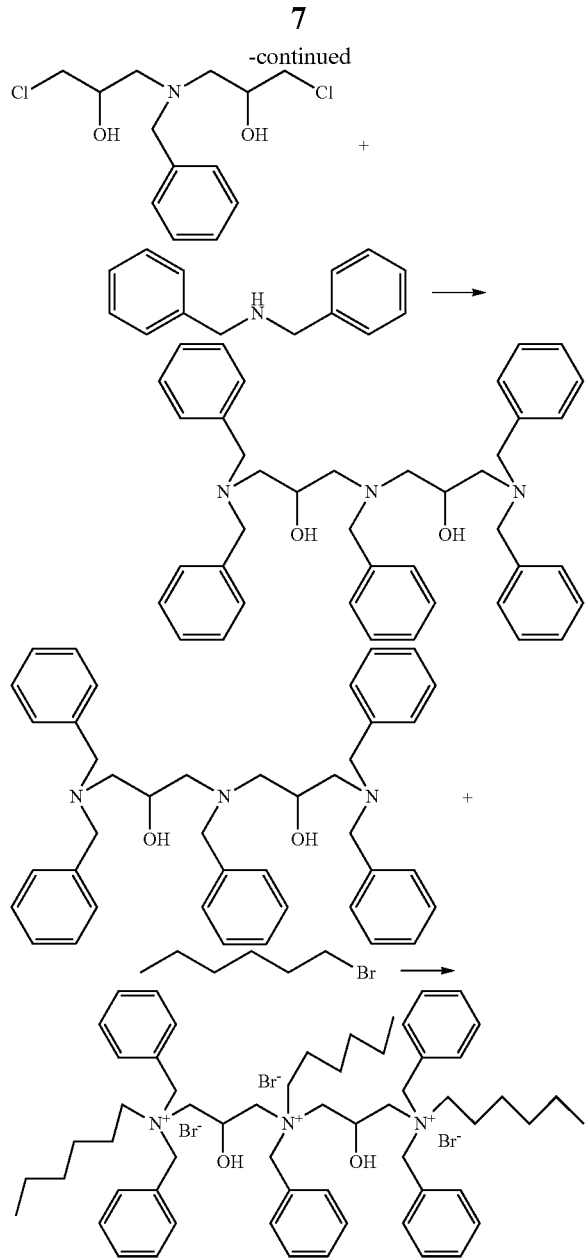

Embodiment 4

A process for preparing a dibenzylaminquaternary ammonium salt high-temperature resistant corrosion inhibitor, comprising the following steps:

(1) Add 12.1 g of phenethylamine to a 250 mL three-necked flask, and add 100 mL of acetonitrile as a solvent at the same time, and then stir them evenly;

(2) Weigh 9.25 g of epichlorohydrin and dissolve in 30 mL of absolute ethanol, stir slowly, then add it to the above phenylethylamine solution dropwise slowly, stir to react at room temperature for 14 h, to obtain an intermediate I after distillation under reduced pressure;

(3) Weigh 2.13 g of intermediate I into a 250 mL three-necked flask, and add 90 mL of absolute ethanol as a solvent at the same time, then stir them evenly; weigh 1.97 g of dibenzylamine and dissolve in 30 mL of absolute ethanol and stir well. Add slowly dropwise to the intermediate I solution, then add 1.6 g of triethylamine, warm to 80° C. for reflux to react 14 h, after the reaction, cool to the room temperature, and perform filtration, extraction and distillation under a reduced pressure to obtain the intermediate II;

(4) Weigh 4.1 g of intermediate II into a 250 mL three-necked flask, add 100 mL of absolute ethanol as a solvent at the same time, then stir them evenly; Weigh 1.26 g of benzyl chloride and slowly add dropwise to the intermediate II solution, then warm to 90° C. for reflux to react 15 h, after the reaction, cool to the room temperature, and perform filtration, extraction and distillation under a reduced pressure to obtain the dibenzylaminquaternary ammonium salt corrosion inhibitor.

Performance Test 1 Determination of Water Solubility of Corrosion Inhibitors

The water solubility of the corrosion inhibitor prepared by Embodiments 1 to 4 and its compatibility with the system containing the iron ion stabilizer, clay stabilizer and discharge aiding agent under 90° C. are determined. The process is as follows: weigh 0.1 of the corrosion inhibitor of the present invention, and dissolve in 200 mL of 20% hydrochloric acid solution, respectively, stir and observe its dissolution. Prepare 20% hydrochloric acid solution system adding with iron ion stabilizer citric acid, clay stabilizer potassium chloride and discharge aiding agent OP-10 or fluorocarbon surfactant, respectively, and then weigh 0.1 g of the corrosion inhibitor of the present invention and add them to the 20% hydrochloric acid solution system, to observe the compatibility. Results are shown in the Table 1 below.

TABLE 1

Test of water solubility and compatibility of different corrosion inhibitors

| Corrosion inhibitor | Water solubility and appearance | Compatibility |
| --- | --- | --- |
| Embodiment 1 | Soluble colorless transparent liquid | Uniform and transparent, no layering |
| Embodiment 2 | Soluble colorless transparent liquid | Uniform and transparent, no layering |
| Embodiment 3 | Soluble colorless transparent liquid | Uniform and transparent, no layering |
| Embodiment 4 | Soluble colorless transparent liquid | Uniform and transparent, no layering |

As shown from table 1, the corrosion inhibitor prepared by the invention has excellent water solubility, and has good compatibility with various addition agents in a high-temperature hydrochloric acid system. The system is uniform and transparent and free of layering.

Performance Test 2 Determination of Corrosion Inhibition Performance of Corrosion Inhibitors The corrosion inhibition performance of corrosion inhibitors in the embodiments 1 to 4 is determined by a 4 h corrosion test at 90° C. using 20% hydrochloric acid as a corrosive medium and P110 carbon steels. The amount of corrosion inhibitors is 1000 ppm. Results are shown in the Table 2.

TABLE 2

Determination of corrosion inhibition performance of all corrosion inhibitors

| Corrosion inhibitor | Corrosion rate ($gm^{-2}h^{-1}$) | Inhibition rate (%) | Surface morphology |
| --- | --- | --- | --- |
| Blank | 724.63 | / | Uneven |
| Embodiment 1 | 34.87 | 95.18 | Smooth and flat |
| Embodiment 2 | 45.79 | 93.68 | Smooth and flat |
| Embodiment 3 | 29.86 | 95.88 | Smooth and flat |
| Embodiment 4 | 24.47 | 96.62 | Smooth and flat |

As shown from the Table 2, the corrosion inhibitors prepared by the method of the present invention have a good corrosion inhibition effect.

In summary, the preparation process of the present invention is simple and feasible. The prepared corrosion inhibitor is ionic and has good water solubility in acid solution. The corrosion inhibitor has obvious inhibitory effect on the corrosion of carbon steels in oil-gas wells at a high temperature of 90° C.; in addition, after cleaning, the hanging pieces are flat and free of obvious pitting corrosion, indicating that the corrosion inhibitors prepared by the invention have the features of acid resistance and high-temperature resistance.

The invention claimed is:

1. A process for preparing a dibenzylamine quaternary ammonium salt high-temperature resistant corrosion inhibitor, comprising the following steps in sequence:
   (1) dissolve amine reagents selected from the group consisting of benzylamine, phenethylamine, morpholine or indole in an organic solvent, slowly add epichlorohydrin dropwise, stir to react at a room temperature for 12-14 hours, and then distill under a reduced pressure, and wash to obtain an intermediate I;
   (2) dissolve the intermediate I in an organic solvent, add dibenzylamine, then add an acid binding agent, warm to 60-80° C. to react for 14 to 16 hours, after cooling to room temperature, perform filtration, extraction and distillation under a reduced pressure to obtain an intermediate II;
   (3) dissolve the intermediate II in an organic solvent, add quaternizing reagent, then warm to 80-110° C. to react for 12 to 15 hours, after cooling to room temperature, perform filtration, extraction and distillation under a reduced pressure to obtain the dibenzylamine quaternary ammonium salt high-temperature resistant corrosion inhibitor.

2. The process for preparing a dibenzylamine quaternary ammonium salt high-temperature resistant corrosion inhibitor according to claim 1, wherein a molar ratio of epichlorohydrin to amine reagents is 1:1-1:3.

3. The process for preparing a dibenzylamine quaternary ammonium salt high-temperature resistant corrosion inhibitor according to claim 1, wherein the organic solvent is acetone, ethanol, or acetonitrile.

4. The process for preparing a dibenzylamine quaternary ammonium salt high-temperature resistant corrosion inhibitor according to claim 1, wherein the acid binding agent is potassium carbonate, sodium hydroxide or triethylamine.

5. The process for preparing a dibenzylamine quaternary ammonium salt high-temperature resistant corrosion inhibitor according to claim 1, wherein a molar ratio of dibenzylamine to the acid binding agent is 1:1-1:2.

6. The process for preparing a dibenzylamine quaternary ammonium salt high-temperature resistant corrosion inhibitor according to claim 1, wherein a molar ratio of dibenzylamine to the intermediate I is 1:1-1:4.

7. The process for preparing a dibenzylamine quaternary ammonium salt high-temperature resistant corrosion inhibitor according to claim 1, wherein the quaternizing reagent is benzyl chloride, chloromethylnaphthalene or bromohexane.

8. The process for preparing a dibenzylamine quaternary ammonium salt high-temperature resistant corrosion inhibitor according to claim 1, wherein a molar ratio of the quaternizing reagent to the intermediate II is 1:1-2:1.

9. A method of inhibiting acid corrosion of carbon steels, comprising:
   applying 1000 ppm of the dibenzylamine quaternary ammonium salt high-temperature resistant corrosion inhibitor according to claim 1 to the carbon steels.

* * * * *